US00PP09478P

United States Patent [19]

Challet

[11] Patent Number: Plant 9,478

[45] Date of Patent: Mar. 19, 1996

[54] CHRYSANTHEMUM PLANT NAMED 'CHARIBO'

[75] Inventor: Jean-Pierre Challet, Lafayette, Calif.

[73] Assignee: Selection New Plant Sarl, Le Cannet des Maures, France

[21] Appl. No.: 273,995

[22] Filed: Jul. 12, 1994

[51] Int. Cl.[6] ..... A01H 5/00

[52] U.S. Cl. ..... Plt./77

[58] Field of Search ..... Plt./77, 82.1

[56] References Cited

U.S. PATENT DOCUMENTS

| | | | |
|---|---|---|---|
| P.P. 3,483 | 2/1974 | Shoesmith | Plt./77 |
| P.P. 3,950 | 9/1976 | Jessel, Jr. et al. | Plt./77 |
| P.P. 4,251 | 5/1978 | Iwasaki | Plt./77 |
| P.P. 4,470 | 10/1979 | Jessel, Jr. et al. | Plt./77 |
| P.P. 5,240 | 6/1984 | Jessel, Jr. et al. | Plt./77 |
| P.P. 6,124 | 3/1988 | Duffett | Plt./77 |

*Primary Examiner*—Howard J. Locker

*Attorney, Agent, or Firm*—Burns, Doane, Swecker & Mathis

[57] ABSTRACT

A new and distinct Chrysanthemum cultivar named 'Charibo' is provided. The new cultivar was the result of a controlled breeding program. Attractive very large double incurved blossoms of the pompon type are formed generally in the shape of a round ball. The response period of the flowers is approximately nine weeks. Recurrent profuse flower production throughout the year is possible. The plant possesses strong stems, forms large deep green leaves, and commonly assumes a height of approximately 40 to 45 cm. The new cultivar is particularly suited for use in the production of a decorative pot Chrysanthemum and can be grown single-stem, disbudded, or center budded. No growth regulator is necessary.

2 Drawing Sheets

SUMMARY OF THE INVENTION

The present invention comprises a new and distinct cultivar of Chrysanthemum, botanically known as *Dendranthema grandiflorum,* and hereinafter is referred to by the cultivar name 'Charibo'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during October 1987 at Nuaille, Trementines, France. The female parent (i.e, the seed parent) was an unnamed plant designated 84-127-5 (non-patented in the United States) having a large white pompon flower that was bred during 1984 which lacked a good response to pinching and had deficient foliage, and the male parent (i.e., the pollen parent) was the 'Le Layon' cultivar (non-patented in the United States) having a large double yellow flat flower that was bred during the 1960's and had a response time of 10 weeks. The parentage of the new cultivar can be summarized as follows:

84-127-5×'Le Layon'.

The seeds resulting from the above pollination were sown and many small plantlets were obtained which were physically and biologically different from each other. Selective study resulted in the identification of a single plant of the new variety.

It was found that the new cultivar of the present invention:

(a) exhibits attractive double incurved white pompon blossoms generally in the shape of a round ball,
(b) exhibits a flower response period of approximately nine weeks,
(c) forms attractive dark green foliage,
(d) achieves a short to medium plant height, and
(e) is particularly suited for pot mum production on a recurrent basis throughout the year.

The new cultivar is intended primarily as a decorative pot Chrysanthemum for growing indoors. However, it also can be grown for cut flower production in those instances where stems of approximately 30 to 40 cm. are acceptable. Also, the new cultivar can be grown outdoors at temperatures above freezing.

In the absence of debudding commonly 6 to 7 blossoms form per stem. The new cultivar can be grown single-stem, with disbudding, or center budded. An increased number of branches readily can be induced by pinching. The pinching of a cutting commonly produces 3 or 4 stems. The plant is somewhat sensitive to over-watering in the winter.

The new cultivar can be considered to be an October-flowering greenhouse variety with the natural flowering season commonly occurring in weeks 42 and 43 of the year. Attractive blossoms can be produced on a recurrent basis throughout the year with the indicated nine week response period. The blossoms are long lasting and commonly can be maintained on the plant for two to three weeks, and for three to four weeks when cut and placed in a vase.

Asexual reproduction of the new cultivar by cuttings initially taken during 1988, as performed in Nuaille, Trementines, France, in a controlled environment has demonstrated that the characteristics of the new cultivar as herein described are firmly fixed and are retained through successive generations of asexual propagation.

'Charibo' has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the 'Cuedolys' cultivar (non-patented in the United States), the 'Charibo' cultivar is found to exhibit a shorter response period of approximately 9 weeks vs. approximately 11 weeks, less incurving of the ray florets, pointed tips of the ray florets vs. emarginate tips, and the immature ray florets are more cream at the center of the blossoms instead of more green. Also, when compared to the 'May Shoesmith' cultivar (non-patented in the United States), the 'Charibo' cultivar is found to exhibit a shorter response period of approximately 9 weeks vs. approximately 11 weeks, and to form a plant having a shorter height.

The new cultivar is being marketed under the HARP trademark.

BRIEF DESCRIPTION OF THE PHOTOGRAPHS

The accompanying photographs were prepared during June 1994, and show as nearly true as it is reasonably possible to make the same in color illustrations of this character, typical plants and plant parts of the new cultivar of the present invention. The plant were 12 weeks of age and were grown at Nuaille, Trementines, France, under standard greenhouse conditions which approximately those commonly utilized for the production of decorative pot mums. The plant had been disbudded in order to encourage the formation of one large bloom per stem. One application of Alar growth regulant was utilized at a concentration of 3 grams per liter. In some photographs a measuring tape is present and can be used for size comparison.

DETAILED DESCRIPTION

Figure 1:
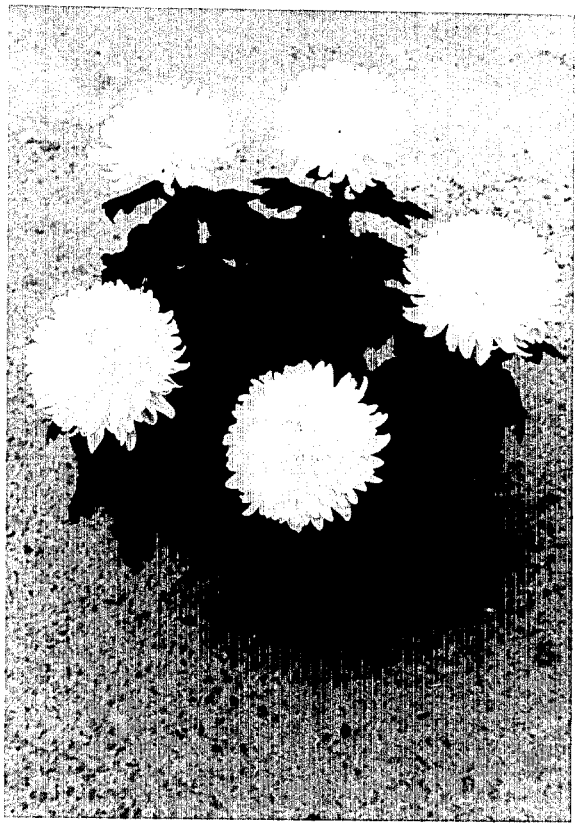
FIG. 1 illustrates typical specimens of the overall plant wherein five cuttings were placed in a 20 cm. pot. The clear white incurved flowers, as well as the foliage, are apparent.
Figure 2:
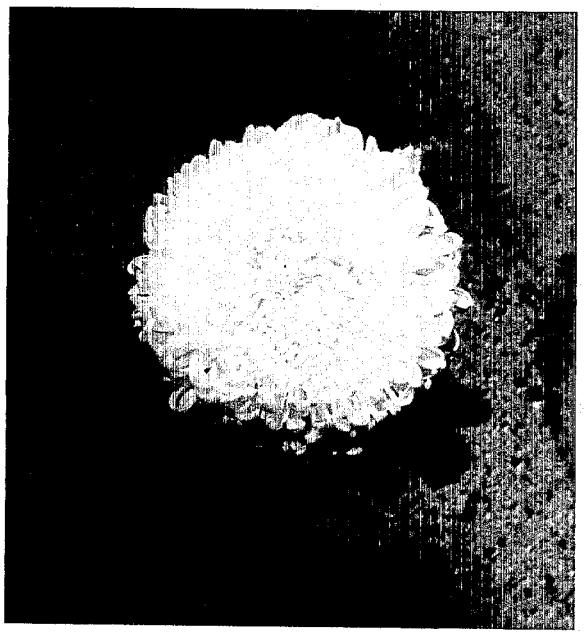
FIG. 2 illustrates a closer view of a typical open flower wherein the more immature center displays a cream-yellow appearance.
Figure 3:
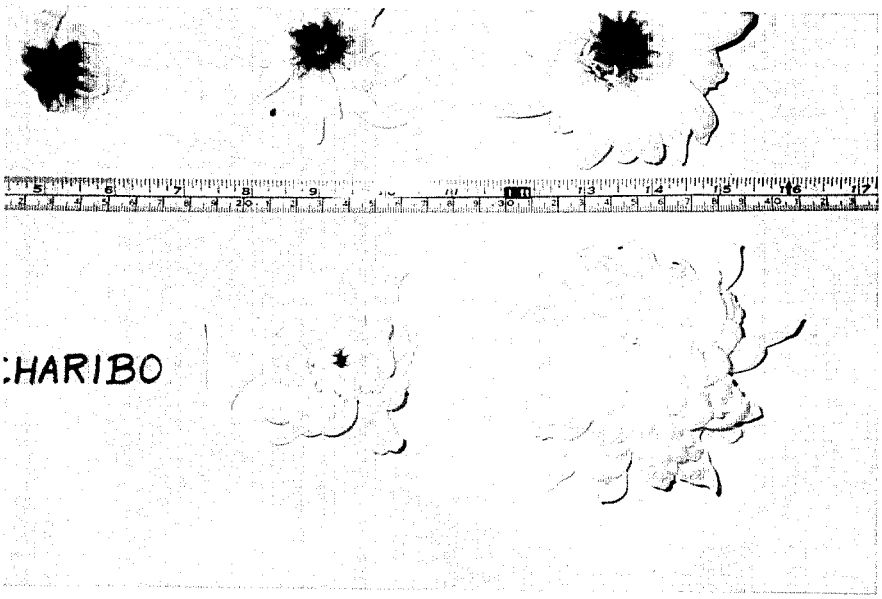
FIG. 3 illustrates above the under surfaces of three flowers in progressive stages of opening from left to right, and below the upper surfaces of a pair of flowers in progressive stages of opening from left to right.
Figure 4:
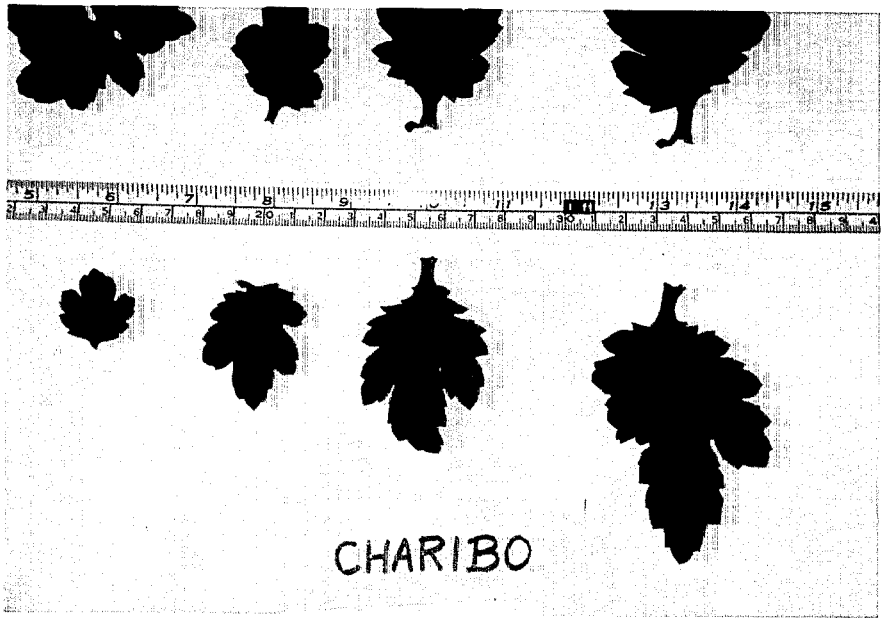
FIG. 4 illustrates at the top row the upper surfaces of typical leaves of various sizes and at the bottom row the under surfaces of typical leaves of various sizes.

The chart used in the identification of colors described hereafter is the R.H.S. Colour Chart of the Royal Horticultural Society, London, England. In some instances more common color terms are provided and are to be accorded their usual dictionary significance. The plants described were 12 weeks of age and were grown at Nuaille, Trementines, France, under standard greenhouse conditions which approximately those commonly utilized for the production of decorative pot mums.

Classification:

*Botanical.—Dendranthema grandiflorum,* cv. 'Charibo' .

*Commercial.*—Decorative pot mum.

Inflorescence

A. Capitulum:

*Form.*—Large, double, incurved. The outside rows of petals may change to a semi-incurved configuration or even a slightly reflexed configuration upon maturity.

*Type.*—Pompon.

*Diameter across face.*—Approximately 15 cm. on average when fully expanded.

B. Corolla of ray and disc florets:

*Color of bud.*—Commonly Yellow-Green Group 150D on the outside.

*Disc florets.*—Tubular, yellow in coloration, few in number, very difficult to observe, and tend to be scattered among the ray florets with a small cluster at the apex of the receptacle that is visible only when the ray florets are removed. Such disc florets are classified as Type 2 pursuant to UPOV reference TG/26/4 of Nov. 14, 1979.

*General tonality.*—At the beginning of flowering the blossoms appear to be bicolored with pure white on the outer rows of ray florets and soft cream to light green on the inner rows of ray florets. The initial bicoloration can be attributed to differences in maturity between the inner rows of ray florets and the outer rows of ray florets. As the blossoms mature, the inner rows of ray florets tend to fade to white, and finally all of the ray florets become white. The rate of fading is influenced by the temperature and light intensity that is experienced which tends to induce a change in color pigmentation.

*Color ray florets.*—The innermost ray florets become White Group 155D, and the outermost ray florets become White Group 155D but whiter. Immature ray florets at the center of the capitulum vary from cream to Yellow-Green Group 145C, and sometimes display a lime-green tint.

*Configuration ray florets.*—Concave in cross section, textured, and possess pointed tips.

C. Reproductive organs:

*Androecium.*—Generally present with most of the disc florets and absent in ray florets.

*Gynoecium.*—Generally present with most disc florets and with most ray florets.

*Pollen.*—Formed in a slight quantity and golden-yellow in coloration.

*Fragrance.*—Typical of Chrysanthemum.

Plant

A. General appearance:

*Height.*—Short to medium, and approximately 40 to 45 cm. in height on average. A shorter plant can be formed when a growth regulator is applied, but the use of such growth regulator is optional.

B. Foliage:

*Color (upper surface).*—Dark green, Green Group 137A.

*Color (under surface).*—Lighter green approaches Green Group 138A.

*Long day leaf count.*—Approximately 24 to 29 leaves per typical stem in a long day crop before the bud occurs.

*Configuration.*—Lobed (as illustrated).

*Texture.*—Fleshy.

*Internode length.*—Very short.

*Stems.*—Thin to medium in diameter, strong, angular in cross section, Yellow-Green Group 146C in coloration, and commonly with anthocyanin coloration at the nodes.

I claim:

1. A new and distinct cultivar of Chrysanthemum plant named 'Charibo', substantially as herein shown and described, which (a) exhibits attractive double incurved white pompom blossoms generally in the shape of a round ball, (b) exhibits a flower response period of approximately nine weeks, (c) forms attractive dark green foliage, (d) achieves a short to medium plant height, and (e) is particularly suited for pot mum production on a recurrent basis throughout the year.

* * * * *